(12) United States Patent
Yoo

(10) Patent No.: US 10,455,337 B2
(45) Date of Patent: Oct. 22, 2019

(54) HEARING AID ALLOWING SELF-HEARING TEST AND FITTING, AND SELF-HEARING TEST AND FITTING SYSTEM USING SAME

(71) Applicant: THE YEOLRIM CO., LTD., Seoul (KR)

(72) Inventor: Jung Gee Yoo, Ansan (KR)

(73) Assignee: The Yeolrim Co., Ltd., Seoul (KR)

( * ) Notice: Subject to any disclaimer, the term of this patent is extended or adjusted under 35 U.S.C. 154(b) by 87 days.

(21) Appl. No.: 15/562,316

(22) PCT Filed: Apr. 4, 2016

(86) PCT No.: PCT/KR2016/003462
§ 371 (c)(1),
(2) Date: Sep. 27, 2017

(87) PCT Pub. No.: WO2016/159739
PCT Pub. Date: Oct. 6, 2016

(65) Prior Publication Data
US 2018/0352351 A1    Dec. 6, 2018

(30) Foreign Application Priority Data
Apr. 3, 2015   (KR) .................. 10-2015-0047297

(51) Int. Cl.
*H04R 25/00* (2006.01)
*A61B 5/00* (2006.01)
*A61B 5/12* (2006.01)

(52) U.S. Cl.
CPC ............. *H04R 25/70* (2013.01); *A61B 5/002* (2013.01); *A61B 5/123* (2013.01); *H04R 25/305* (2013.01);
(Continued)

(58) Field of Classification Search
CPC ............................ H04R 25/70; H04R 2225/55
See application file for complete search history.

(56) References Cited

U.S. PATENT DOCUMENTS 6,118,877 A * 9/2000 Lindemann ............ H04R 25/70
381/23.1
7,239,711 B1 * 7/2007 Andersen ............... H04R 25/70
381/312
(Continued)

FOREIGN PATENT DOCUMENTS

KR   10-2005-0109323   11/2005
KR   10-2009-0102127    9/2009
(Continued)

OTHER PUBLICATIONS

Korean Written Opinion dated Aug. 11, 2015 in corresponding Korean Application No. 10-2015-0047297.
(Continued)

*Primary Examiner* — Curtis A Kuntz
*Assistant Examiner* — Ryan Robinson
(74) *Attorney, Agent, or Firm* — Faegre Baker Daniels LLP

(57) ABSTRACT

The present invention relates to a hearing aid allowing a self-hearing test and fitting, and a self-hearing test and fitting system using the same. The hearing aid comprises: a signal generating unit for receiving a command from an external terminal and enabling a receiver to generate a signal having a predetermined size and a predetermined frequency; a hearing storing unit for receiving information on whether a user can hear a signal generated by the signal generating unit and storing the user's hearing; and a fitting unit for adjusting an output of a sound according to the user's hearing. The hearing aid enables an accurate measurement of hearing to be made by directly measuring a user's hearing through the hearing aid, hearing measurement to be easily performed from time to time, and fitting of the hearing aid according to the user's hearing to be automatically made. The self-hearing test and fitting system comprises the hearing aid and a control terminal including a connection sensing unit, a
(Continued)

hearing test unit, and an accurate fitting unit, and enables a more accurate control of the hearing aid sound to be made on the basis of the user's hearing.

9 Claims, 10 Drawing Sheets

(52) U.S. Cl.
CPC .......... *H04R 25/505* (2013.01); *H04R 25/554* (2013.01); *H04R 2225/55* (2013.01)

(56) References Cited

U.S. PATENT DOCUMENTS

| | | | | |
|---|---|---|---|---|
| 7,933,419 | B2* | 4/2011 | Roeck | H04R 25/70 |
| | | | | 381/314 |
| 8,675,900 | B2* | 3/2014 | Anderson | A61B 5/121 |
| | | | | 381/314 |
| 9,107,016 | B2* | 8/2015 | Shennib | H04R 25/70 |
| 2010/0284556 | A1* | 11/2010 | Young | H04R 25/558 |
| | | | | 381/314 |
| 2012/0177212 | A1* | 7/2012 | Hou | H04R 25/70 |
| | | | | 381/60 |

FOREIGN PATENT DOCUMENTS

| | | |
|---|---|---|
| KR | 10-0974153 | 8/2010 |
| KR | 10-2013-0047903 | 5/2013 |
| KR | 10-2014-0006668 | 1/2014 |

OTHER PUBLICATIONS

International Search Report dated Jun. 30, 2016 in corresponding PCT Application No. PCT/KR2016/003462.

* cited by examiner though the general description of the invention above is exhaustive, it is not meant to limit the scope of the hearing aid ...

HEARING AID ALLOWING SELF-HEARING TEST AND FITTING, AND SELF-HEARING TEST AND FITTING SYSTEM USING SAME

CROSS-REFERENCE TO RELATED APPLICATIONS

This application is a U.S. National Phase filing of PCT/KR2016/003462, filed Apr. 4, 2016, which claims the benefit of Korean Application No. KR10-2015-0047297, filed Apr. 3, 2015, the entire disclosures of both of which are hereby expressly incorporated by reference herein.

TECHNICAL FIELD

The present invention relates to a hearing aid allowing a self-hearing test and fitting, and a self-hearing test and fitting system using the same. The hearing aid comprises a signal generating unit for receiving a command from an external terminal and enabling a receiver to generate a signal of a predetermined frequency with a predetermined magnitude; a hearing storing unit receiving audibility of the signal generated by the signal generating unit and storing the user's hearing ability; and a fitting unit fitting an output of a sound according to the user's hearing ability, thereby the hearing ability of the user is directly measured by the hearing aid, accurate hearing measurement can be performed, the hearing measurement can be easily performed from time to time, and fitting of the hearing aid according to the user's hearing can be automatically made. The self-hearing test and fitting system comprises the hearing aid and a control terminal including a connection sensing unit, a hearing test unit, and a precise fitting unit, thereby further accurate control of the hearing aid sound can be performed on the basis of the user's hearing ability.

BACKGROUND ART

Now, several million people around world are suffering from hearing impediment, a lot of people among them do not recognize their hearing impediment. Loss of hearing may be caused by several factors including an age, a health, a job, an injury and a disease. The loss of hearing reduces quality of life, deteriorates relationship and obstructs the getting a job. Recently, people who have difficulty in hearing are increased caused by using sound appliances, increasing a percentage of old people and noise environment, thereby demand for a hearing aid is rapidly increased and development of the hearing aid with high performance capable of applying various noise environment is accelerated.

A fitting operation is implemented on a common hearing aid such that the hearing aid provides optimal sound in accordance with a user of the hearing aid. Heretofore, a hearing test is performed prior using additional hearing tester and then the fitting operation is implemented. And, an ordinary seller of hearing aids implements the fitting operation using the hearing tester at an agency on the basis of hearing data which was measured by the hearing tester. As shown in FIG. 1, operations such as a gaining per channels, a compress rate, a noise deduction, a feedback elimination are implemented by a complex program (P).

It cannot consider characteristics of user's ears and the hearing aid that the user's hearing ability is measured by an additional hearing tester to use as hearing measurement information in the fitting operation. Because the fitting is implemented on the basis of hearing data measured by additional hearing tester in accordance with a standard mode in spite that user's ears and a hearing aid have inherent sound characteristics. A fitting is implemented without applying sound around real circumstance because the fitting operation is usually implemented at a quiet agency. Therefore, it is impossible to accept optimal sound through the hearing aid. The following patent discloses fitting on the basis of user's hearing characteristics, however, the hearing test is implemented without hearing aid on. Therefore, it cannot be achieved that hearing test and fitting operation are implemented easily and accurately with considering user's hearing ability and a variation of environment.

CONVENTIONAL ART

Korea Laid-open Patent Publication No. 10-2014-0098615 'Method for fitting hearing aid connected to mobile terminal and mobile terminal performing thereof'

DISCLOSURE

Technical Problem

The present invention contrives in order to solve the above problem.

The present invention relates to a hearing aid including a microphone being input external sounds, a signal processor processing a signal input from the microphone, a receiver reproducing a signal processed by the signal processor, and a memory storing various data necessary for operation of the hearing aid. The present invention provides a hearing aid allowing self-hearing test and fitting. The hearing aid includes a wireless communication unit communicating wireless signal with an external terminal, a signal generating unit receiving a command from the external terminal and having the receiver generating a signal of a predetermined frequency with a predetermined magnitude, a hearing storing unit receiving from the external terminal audibility of the signal generated from the signal generating unit to store user's hearing ability, thereby user's hearing ability is measured directly with the hearing aid to accomplish accurate hearing measurement and the hearing measurement can be performed easily at any time.

The present invention provides a hearing aid allowing self-hearing test and fitting. The hearing aid includes a hearing storing unit having a minimum audible value storing module which stores minimum audible signal audible to a hearing aid user and a maximum audible value storing module which stores maximum audible signal audible to a hearing aid user without discomfort, thereby measuring hearing range audible to the user.

The present invention provides a hearing aid allowing self-hearing test and fitting. The hearing aid includes a fitting unit fitting output of sounds in accordance with user's hearing ability which is stored in the hearing storing unit, thereby sounds within an audible range for the user, i.e., sounds within user's hearing ability, is output The present invention provides a hearing aid allowing self-hearing test and fitting. The hearing aid includes a fitting unit which includes a basic parameter value setting module setting output parameters of the hearing aid in accordance with the average value of a minimum audible value and a maximum audible value stored by a minimum audible value storing module and a maximum audible value storing module, thereby sounds are output after being fitted automatically at appropriate sounds within an audible range for an user.

The present invention provides a hearing aid allowing self-hearing test and fitting. The hearing aid includes a signal variation module having a signal generating by frequency module which is generating signals for each frequency and a signal variation module which increases or decreases the signals generated for each frequency at regular intervals, thereby it is possible to measure user's hearing ability at each frequency and perform a hearing measurement easily.

The present invention provides a self-hearing test and fitting system using a user's terminal, a tablet or PC and so on. The system includes a hearing aid receiving sounds around circumstance and to transmit after transforming audible sounds for a user; and a control terminal capable of communicating with the hearing aid and transmitting audibility of the sounds from the hearing aid.

The present invention provides a self-hearing test and fitting system capable of sensing connectivity with a hearing aid and performing a hearing test automatically. The system includes a control terminal which has a connection sensor sensing connectivity with the hearing aid and a hearing test unit transmitting audibility of signals from the hearing aid to test user's hearing ability.

The present invention provides a self-hearing test and fitting system of which users can easily implement a hearing test by themselves using sounds from the hearing aid and select audibility by themselves to perform accurate hearing measurement. The system includes a hearing test unit having an audibility input module. The audibility input module includes an inaudible signal input module which inputs an inaudibility (i.e., the inaudibility indicates that sounds from the signal generating unit is not heard), an audible signal input module which inputs an audibility (i.e., the audibility indicates that sounds from the signal generating unit is heard) and an excessive signal input module which inputs an excessiveness (i.e., the excessiveness indicates that sounds from the signal generating unit is excessive).

The present invention provides a self-hearing test and fitting system. The system includes a hearing test unit which has a magnitude interval adjusting module adjusting a magnitude interval of a signal generated from the signal generating unit and a frequency interval adjusting module adjusting a frequency interval of the signal generated from the signal generating unit, thereby adjusting balance of accuracy and promptness of a hearing test to perform a quick hearing test or an accurate hearing test according to circumstances.

The present invention provides a self-hearing test and fitting system. The system includes a hearing test unit which includes a search start module searching hearing test information stored in a memory of an hearing aid and determining a start of hearing test in accordance with existence of the hearing test information, thereby the hearing test is automatically performed if the hearing test has not been performed and the hearing test is left out when the hearing test has been performed already.

The present invention provides a self-hearing test and fitting system. The system includes a control terminal which has a precise fitting unit allowing precise fitting. A hearing test unit stores in a hearing aid a minimum audible value audible to a hearing aid user and a maximum audible value audible without discomfort. The precise fitting unit selects the most audible sound between the minimum audible value and the maximum audible value, thereby it is possible to adjust sounds of the hearing aid more precisely.

The present invention provides a self-hearing test and fitting system. The system includes a precise fitting unit which has a frequency selection module selecting a frequency, a volume variation module increasing or decreasing a volume of a frequency selected from the frequency selection module and an optimum selection module selecting the most audible sound. The fitting unit of the hearing aid includes a precise parameter value setting module which sets precise parameter values according to volumes selected by the optimum selection module, thereby providing the user with optimum sounds.

Technical Solution

In order to solve the above objects, the present invention is embodied by embodiments with following components.

According to an embodiment of the present invention, a hearing aid according to the present invention includes a microphone being input external sounds, a signal processor processing a signal input from the microphone, a receiver reproducing a signal processed by the signal processor, a memory storing various data necessary for operation of the hearing aid, a wireless communication unit communicating wireless signal with an external terminal, a signal generating unit receiving a command from the external terminal and enabling the receiver to generate a signal of a predetermined frequency with a predetermined magnitude, and a hearing storing unit receiving from the external terminal audibility of the signal generated from the signal generating unit and storing user's hearing ability, thereby allowing measurement of user's hearing ability.

According to another embodiment of present invention, the hearing storing unit of the hearing aid allowing self-hearing test and fitting according to the present invention includes a minimum audible value storing module which stores a minimum audible signal audible to the user of the hearing aid and a maximum audible value storing module which stores a maximum audible signal audible to the user without discomfort.

According to another embodiment of the present invention, the hearing aid allowing self-hearing test and fitting according to the present invention includes a fitting unit which adjusts output of the sound in accordance with user's hearing ability stored in the hearing storing unit.

According to another embodiment of the present invention, the fitting unit of the hearing aid allowing self-hearing test and fitting according to the present invention includes a basic parameter value setting module which sets output parameters of the hearing aid in accordance with the average value of a maximum audible value and a minimum audible value stored by a maximum audible value storing module and a minimum audible value storing module.

According to another embodiment of the present invention, the signal generating unit of the hearing aid allowing self-hearing test and fitting according to the present invention includes a signal generating by frequency module which generates signals for each frequency and a signal variation module which increases or decreases magnitude of signals generated for each frequency at regular intervals.

According to another embodiment of the present invention, a self-hearing test and fitting system according to the present invention includes a hearing aid receiving sounds around circumstance and transmitting after transforming audible sounds for a user; and a control terminal capable of communicating with the hearing aid and transmitting audibility of the sounds from the hearing aid.

According to another embodiment of the present invention, the control terminal of the self-hearing test and fitting system according to the present invention includes a connection sensor sensing connectivity with the hearing aid and a hearing test unit transmitting audibility of signals from the hearing aid to test user's hearing ability.

According to another embodiment of the present invention, the hearing test unit of the self-hearing test and fitting system according to the present invention includes an audibility input module which inputs audibility of the sounds generated from the signal generating unit, the audibility input module includes an inaudible signal input module which inputs an inaudibility (i.e., sounds from the signal generating unit is not audible), an audible signal input module which inputs an audibility (i.e., sounds from the signal generating unit is audible) and an excessive signal input module which inputs an excessiveness (i.e., sounds from the signal generating unit is excessive).

According to another embodiment of the present invention, the hearing test unit of the self-hearing test and fitting system according to the present invention includes a magnitude interval adjusting module adjusting a magnitude interval of a signal generated from the signal generating unit and a frequency interval adjusting module adjusting a frequency interval of the signal generated from the signal generating unit.

According to another embodiment of the present invention, the hearing test unit of the self-hearing test and fitting system according to the present invention includes a search start module searching hearing test information stored in a memory of the hearing aid and determining a start of hearing test in accordance with existence of the hearing test information.

According to another embodiment of the present invention, the control terminal of the self-hearing test and fitting system according to the present invention includes a precise fitting unit allowing precise fitting for the hearing aid, the hearing test unit stores in a hearing aid a minimum audible value audible to a hearing aid user and a maximum audible value audible without discomfort, and the precise fitting unit selects the most audible sound between the minimum audible value and the maximum audible value.

According to another embodiment of the present invention, the precise fitting unit of the self-hearing test and fitting system according to the present invention includes a frequency selection module selecting a frequency, a volume variation module increasing or decreasing a volume of a frequency selected from the frequency selection module and an optimum selection module selecting the most audible sound, and the fitting unit of the hearing aid includes a precise parameter value setting module which sets precise parameter values according to volumes selected by the optimum selection module.

Advantageous Effects

The present invention provides following effects from the above embodiments, and components, combination and usage relationship as follows.

The present invention relates to a hearing aid including a microphone being input external sounds, a signal processor processing a signal input from the microphone, a receiver reproducing a signal processed by the signal processor and a memory storing various data necessary for operation of the hearing aid. The present invention provides a hearing aid allowing self-hearing test and fitting including a wireless communication unit communicating wireless signal with an external terminal, a signal generating unit receiving a command from the external terminal and having the receiver generating a signal with a predetermined magnitude at a predetermined frequency, a hearing storing unit receiving from the external terminal whether the signal generated from the signal generating unit is audible or not and storing user's hearing ability, thereby user's hearing ability can be measured directly with the hearing aid to accomplish accurate hearing measurement and the hearing measurement can be performed easily at any time.

The present invention provides a hearing aid allowing self-hearing test and fitting including a hearing storing unit which has a minimum hearing value storing module storing minimum hearing signal audible to a hearing aid user and a maximum hearing value storing module storing maximum hearing signal audible to a hearing aid user without discomfort, thereby measuring hearing range audible to the user.

The present invention provides a hearing aid allowing self-hearing test and fitting including a fitting unit which fits output of sounds in accordance with user's hearing ability stored in the hearing storing unit, thereby sounds from the hearing aid can output within a range audible to user (that is sounds within user's hearing ability) to prevent inaudible or discomfort caused by too low sounds or too loud sounds.

The present invention includes a fitting unit which includes a basic parameter value setting module setting output parameters of the hearing aid in accordance with the average value of a minimum audible value and a maximum audible value stored by a minimum audible value storing module and a maximum audible value storing module, thereby sounds can be output after being adjusted automatically at appropriate sounds within an audible range for an user.

The present invention includes a signal generating unit which has a signal generating by frequency module generating signals for each frequency and a signal variation module increasing or decreasing the signals generated for each frequency at regular intervals, thereby it is possible to measure user's hearing ability at each frequency and perform a hearing measurement easily.

The present invention includes a hearing aid receiving sounds around circumstance and transmitting after transforming audible sounds for an user; and a control terminal capable of communicating with the hearing aid and transmitting audibility of the sounds from the hearing aid, thereby it is possible to perform the hearing test and fitting using a user's terminal, a tablet or PC and so on.

The present invention includes a control terminal which has a connection sensor sensing connectivity with the hearing aid and a hearing test unit transmitting audibility of signals from the hearing aid to test user's hearing ability, thereby it is possible to sense connectivity with a hearing aid and perform a hearing test automatically.

The present invention includes a hearing test unit having an audibility input module. The audibility input module includes an inaudible signal input module which inputs inaudibility (i.e., sounds from the signal generating unit is not heard) and an audible signal input module which inputs audibility (i.e., sounds from the signal generating unit is heard) and an excessive signal input module which inputs excessiveness (i.e., sounds from the signal generating unit is excessive), thereby it is possible to implement easily a hearing test by themselves using sounds from the hearing aid and select audibility by themselves to perform accurate hearing measurement.

The present invention includes a hearing test unit which has a magnitude interval adjusting module adjusting a magnitude interval of a signal generated from the signal generating unit and a frequency interval adjusting module adjusting a frequency interval of the signal generated from the signal generating unit, thereby adjusting balance of accuracy and promptness of a hearing test to perform a quick hearing test or an accurate hearing test according to circumstances.

The present invention includes a hearing test unit which includes a search start module searching hearing test information stored in a memory of an hearing aid and determining a start of hearing test in accordance with existence of the hearing test information, thereby the hearing test is automatically performed if the hearing test has not been performed and the hearing test is left out when the hearing test has been performed already.

The present invention includes a control terminal which has a precise fitting unit capable of precise fitting. The hearing test unit stores in a hearing aid a minimum audible value audible to a hearing aid user and a maximum audible value audible without discomfort, and the precise fitting unit selects the most audible sound between the minimum audible value and the maximum audible value to adjust sounds of the hearing aid more precisely.

The present invention includes a precise fitting unit which includes a frequency selection module selecting a frequency, a volume variation module tuning a volume of a frequency selected from the frequency selection module and an optimum selection module selecting the most audible sound, the fitting unit of the hearing aid includes a precise parameter value setting module which sets precise parameter values according to volumes selected by the optimum selection module, thereby providing the user with optimum sounds.

| | |
|---|---|
| 1: Hearing aid | 11: Microphone 1 |
| 2: Signal processor | 13: Receiver |
| 14: Memory | 15: Wireless communication unit |
| 16: Signal generating unit | 161: Signal generating by frequency module |
| 163: Signal variation module | |
| 171: Minimum audible value storing module | 17: Hearing storing unit |
| 173: Maximum audible value storing module | 181: Basic parameter value setting module |
| 18: Fitting unit | |
| 183: Precise parameter value setting module | 31: Connection sensing unit |
| 3: Control terminal | 331: Test start module |
| 33: Hearing test unit | 331b: Manual start module |
| 331a: Auto start module | 333a: Non-hearing signal input module |
| 333: Hearing input module | 333c: Excessive signal input module |
| 333b: Hearing signal input module | 351: Frequency selection module |
| 335: Magnitude interval adjusting module | 355: Optimum selection module |
| 337: Frequency interval adjusting module | 37: Wireless communication unit |
| 35: Precise fitting unit | |
| 353: Magnitude variation module | |
| 357: Variation width adjusting module | |

BEST MODE

Embodiments according to the present invention of a hearing aid allowing self-hearing test and fitting, and self-hearing test and fitting system using the same will now be described with reference to the accompanying drawings for explaining. In describing the present invention, descriptions for universally known elements or functions may be left out when the descriptions make obscure essential points of the inventive concepts. In the entire description, other components are not excluded but further includes another component when a part includes a component, unless otherwise provided for.

Figure 1:
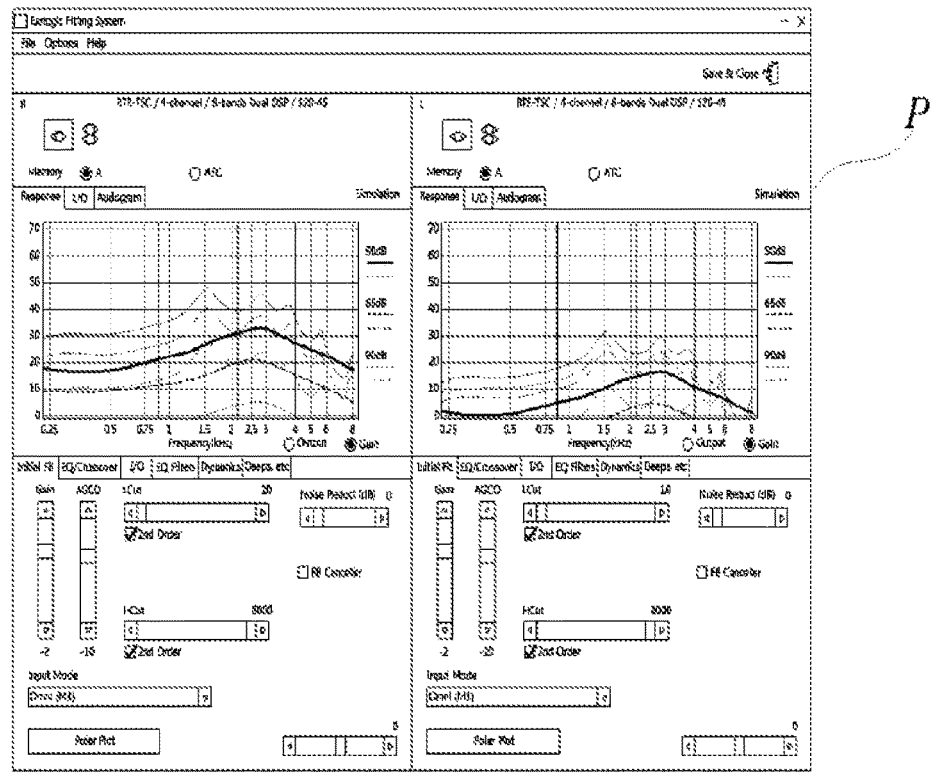
FIG. 1 is a reference drawing illustrating an example of conventional hearing aid fitting program.
Figure 2:
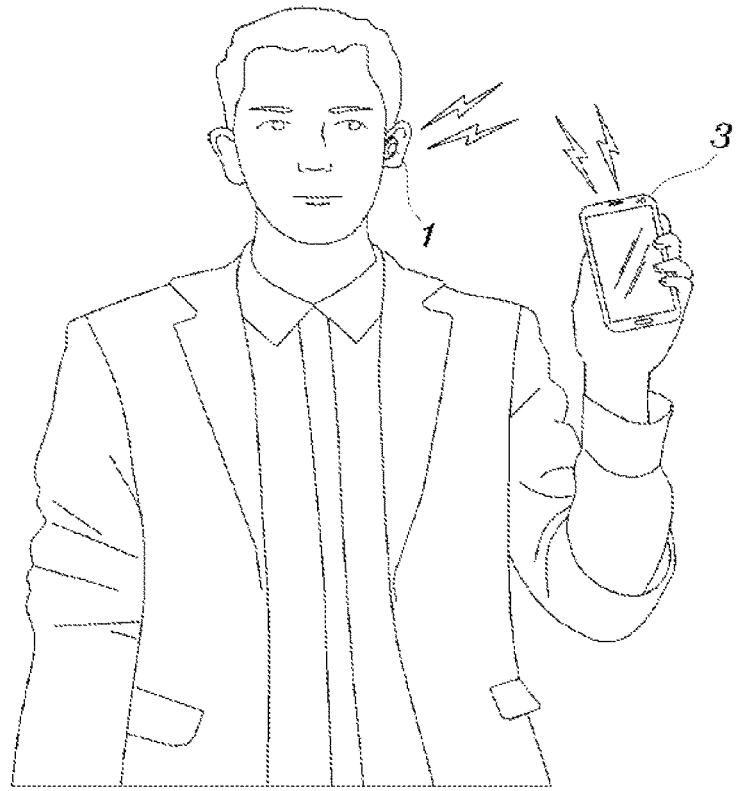
FIG. 2 is a structure drawing illustrating self-hearing test and fitting systems according to an embodiment of the present invention.

Referring to FIGS. 2 through 12, a self-hearing test and fitting system according to an embodiment of the present invention is described. The self-hearing test and fitting system includes a hearing aid 1 which receives circumference sounds and transmits the sound after transforming into audible sounds for user; and a control terminal 3 which is capable of communication with the hearing aid 1 and transmits audibility of the sounds from the hearing aid 1 to the hearing aid 1. As described in the background description, user's hearing ability is measured with an additional hearing tester and a seller of hearing aids implements the fitting of a hearing aid at an agency with complex program as shown in FIG. 1 with reference to hearing test data. The fitting means adjusting sounds of a hearing aid in consideration of different hearing characteristics for users. Thus the fitting cannot performed in consideration of user and hearing aid characteristics because the hearing test for user and the fitting of a hearing aid are implemented separately. In addition, users of hearing aids are generally people with problem on hearing ability or old people. In spite that hearing ability is changing continuously, hearing measurement should be conducted at a hospital or an agency. As conducting the fitting of hearing aid at the agency, the fitting is conducted at different condition from actual use environments thereby optimum sounds cannot be heard at actual use environments. The self-hearing test and fitting system allows the user's hearing measurement with the hearing aid on to accomplish accurate hearing aid in consideration of an individual hearing characteristic and a characteristic of the hearing aid, and allows user to perform easily the measurement of the hearing ability and fitting using their smart phone, a tablet or PC thereby the hearing measurement and fitting can be conducted frequently in accordance with hearing ability and use environments. Thus the user of the hearing aid can experience sounds which is optimized on their hearing ability and use environments.

The hearing aid 1 is worn on user's ear, input sounds of circumstance to transform into sounds audible to user. The hearing aid 1 can be fitted and measure hearing ability in accordance with control of the control terminal 3, and includes a microphone 11 being input external sounds, a signal processor 12 processing a signal input through the microphone 11, a receiver 13 reproducing the signal processed by the signal processor 12 and a memory 14 storing various information necessary to operation of the hearing aid 1, a wireless communication unit 15 communicating wireless signals with the control terminal 3, a signal generating unit 16 receiving a command from the control terminal 3 to let the receiver 13 generating a signal with predetermined magnitude at a predetermined frequency, a hearing storing unit 17 receiving from the external terminal 3 audibility of the signal generated from the signal generating unit 16 and storing user's hearing ability, and fitting unit 18 fitting output of sounds in accordance with user's hearing ability stored by the hearing aid 17.

The microphone 11 is disposed on exterior of the hearing aid which is worn on user's ear to receive analog signal around the ear and transmit the signal to the signal processor 12.

The signal processor 12 transform the analog sound signal received from the microphone 11 into a digital signal, and transform the signal into analog signal after performing a noise removal, a feedback control, a nonlinear amplification and so on, and transmit to the receiver 13. The signal processor 12 may have an analog to digital converter ADC, a digital signal processor DSP, a digital to analog converter DAC. The signal processor 12 can control an output range of sounds from the receiver 13 within a minimum audible value and a maximum audible value in accordance with the user's hearing ability stored by the hearing storing unit 17, i.e., the minimum audible value which is sounds per frequency audible to a hearing aid user and the maximum audible value. The signal processor 12 may control to output sounds in accordance with a basic parameter value or a precise parameter value set by the fitting unit 18. This will be described hereinafter.

The receiver 13 reproduces the analog signal received from the signal processor 12 into audible sounds to let user hearing, and transmit the signal generated by the signal generating unit 16 to user thereby user hearing ability test is available.

The memory 14 is a component to store various information necessary for operation of the hearing aid, and stores the minimum audible value, and the minimum audible value by a minimum audible value storing module 171 and a maximum audible value storing module 173, and stores the basic parameter value and the precise parameter value set by a basic parameter value setting module 181 and a precise parameter value setting module 183.

The wireless communication unit 15 is a component to communicate with the control terminal 3 and may be various types of wireless communication modules such as a Bluetooth, a BLE (Bluetooth Low Energy), a WIFI and so on The hearing aid 1 can be sensed by the control terminal 3 to control the signal generating unit 16, and a hearing test for user and fitting can be performed in accordance with a selection of the control terminal 3. This will be described hereinafter.

Figure 5:
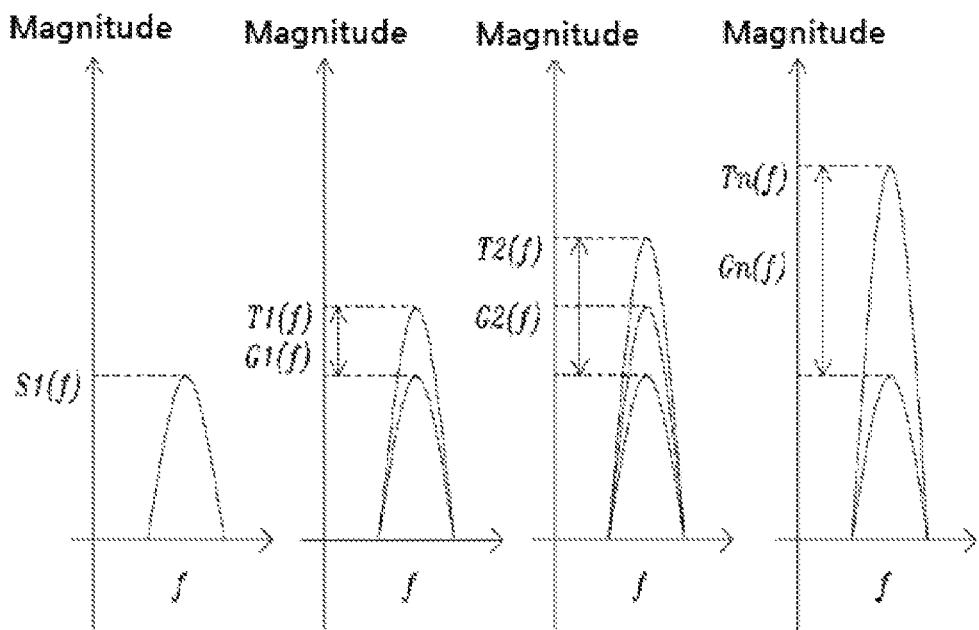
FIG. 5 is a reference drawing illustrating an operation of a signal generating unit of FIG. 3.

The signal generating unit 16 controls the receiver 13 to generate a signal of a predetermined frequency with a predetermined magnitude such that the user's hearing ability is measured, and controls a precise fitting unit 35 of the control terminal 3 to genera a signal such that a precise fitting is accomplished, The signal generating unit 16 may have additional circuit for generating the signal or software embedded therein to generate the signal. The signal generating unit 16 may generate the signal at a form of sound source. The signal generating unit 16 outputs, as shown in FIG. 5, sound signals of $T1(f), T2(f), \ldots Tn(f)$ which is increased at an regular interval such as $G1(f), G2(f), \ldots Gn(f)$ from the minimum sound signal audible to common people at a specific frequency. (For instance, $Tn(f)=G1(f)+Gn(f)$ in the Log scale calculation). Although the sound may be output as decreasing from a loud sound, it is preferable to increase sound from low signal for caring ears and measuring the hearing ability precisely. As hearing sounds generated from the signal generating unit 16, the user of the hearing aid selects whether the sound is audible or not, or too loud by using a audibility input module 333 of the control terminal 3, and transmits that to the hearing aid 1. The volume of the sound is increased when inaudible signal that is not audible or an audible signal that is audible according to the signal input from the control terminal 3 is inputted, and the volume is not increased and the frequency is changed and the previous process is repeated when an excessive signal is input and transmitted from the control terminal 3. The signal value of the sound is stored in the memory 14 as user's hearing information by the hearing storing unit 17 in accordance with the signal input from the control terminal 3, and the rage of output is limited as described above. The signal generating unit 16 includes a signal generating by frequency module 161 which outputs sounds with alternating frequencies and a signal variation module 163 which outputs sounds of regular intervals in accordance with frequencies.

The signal generating by frequency module 161 is a component for outputting sounds by frequency and outputs sounds by regular intervals, for example at 500 Hz, 1 kHz, 2 kHz and etc. If the excessive signal from the control terminal 3, the signal generating by frequency module 161 changes frequency to output sounds of regular intervals after starting from the minimum signal audible to common people. The frequency interval of the sound may be adjusted by a frequency interval adjusting module 337 of the control terminal 3. It depends on performance of the hearing aid 1 such as a frequency channel. More detailed and accurate sounds can be output if it is possible to adjust the frequency interval at more narrowly. Thus, the signal generating by frequency module 161 sets the minimum audible value and the maximum audible value by frequencies such that hearing ability is measured, the output range of the hearing aid is limited and parameter values for user's hearing ability are set to output sounds within user's hearing range. This will be described hereinafter.

The signal variation module 163 is a component to output signals of regular intervals at a predetermined frequency (f) sequentially. A signal increased or decreased in accordance with the signal input from the control terminal 3 is output when a minimum audible to common people at a predetermined frequency is output by the signal variation module by frequency 151. As described above, it is preferable that the signal variation module 163 outputs a sound signal gradually increased from the minimum signal audible to common people. It will be described as an example that the sound signal is increasing gradually to output. The signal variation module 163 outputs signal gradually increased at a regular interval if the inaudible signal or the audible signal from the control terminal 3, or interrupts increasing of the sound, changes the frequency by the signal variation module by frequency 161 and outputs the initial signal again. The magnitude interval of the signals increased or decreased by the signal variation module 163 may be changed by a magnitude interval adjusting module 335 of the control terminal 3. It is possible to measure the user's hearing ability more accurately as narrowing the magnitude intervals. If the signal variation module 163 outputs increasing signal for an example, as described above, a volume at an initial input audible signal is the minimum audible value of the hearing aid user at a corresponding frequency and a volume at an excessive input signal is the maximum audible value of the hearing aid user at a corresponding frequency. Thus, it is possible to output an appropriated sounds audible to users after setting the range of sound audible to the hearing aid user, i.e., the hearing ability of the hearing aid user, limiting the output range between the minimum audible value and the maximum audible value, and setting the basic parameter values.

Figure 6:
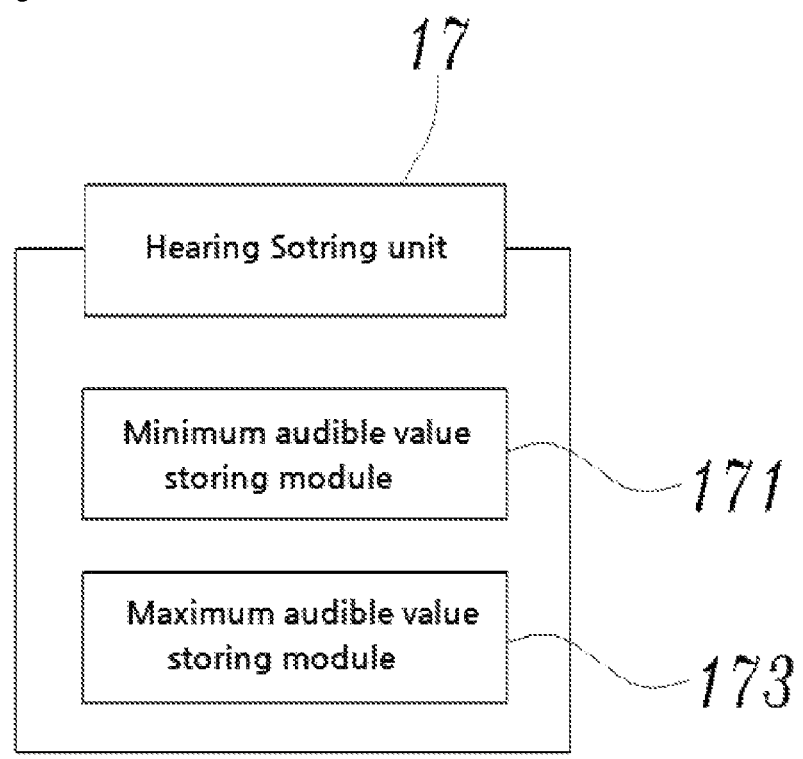
FIG. 6 is a block diagram illustrating a hearing storing unit of FIG. 3.
Figure 7:
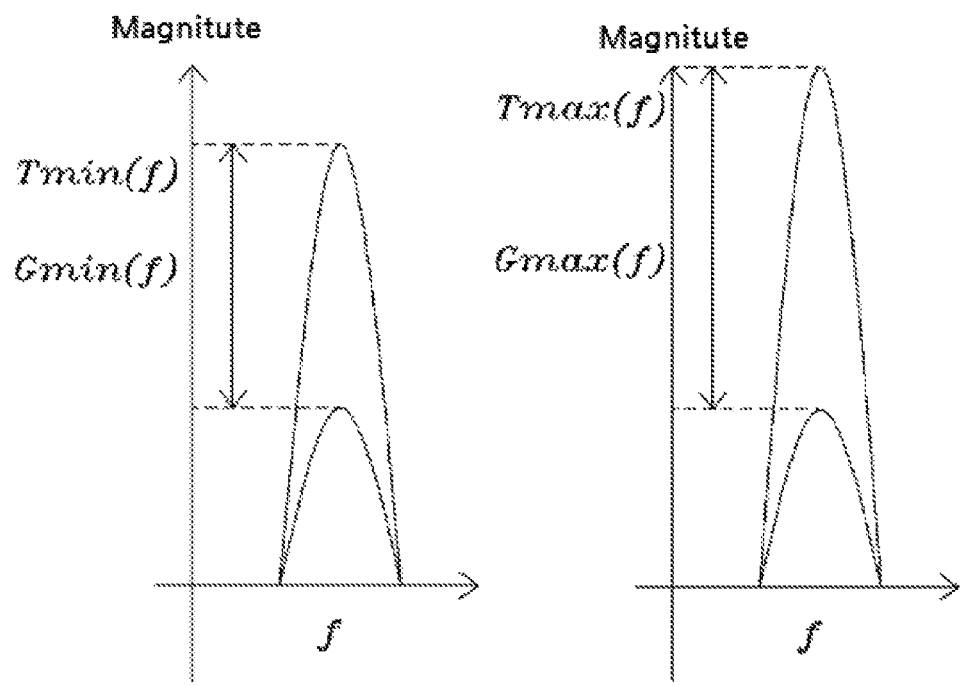
FIG. 7 is a reference drawing illustrating an operation of a hearing storing unit of FIG. 3.

The hearing storing unit 17 is a component to store in the memory 14 the user's hearing ability which is measured by the signal generating unit 16, more accurately, by a hearing test unit 33 of the control terminal 3. As shown in FIG. 6, the hearing storing unit 17 includes a minimum audible value storing module 171 storing minimum audible signal audible to the hearing aid user and a maximum audible value storing module 173 storing a maximum audible signal audible to the hearing aid user without discomfort.

The minimum audible value storing module 171 is a component to store a magnitude of minimum signal audible to the hearing aid user, allows the magnitude by frequency. As described above, the minimum audible value audible to the hearing aid user means a volume of sound at initial input audible signal of the control terminal 3 when the signal variation module 163 outputs signal with gradually increasing magnitude, is a magnitude value of Tmin(f) in FIG. 7. The sound signal at a corresponding frequency is output after always correcting above the minimum audible value such that the user can hear every sounds. The minimum audible value stored by the minimum audible value storing module 171 is stored in the memory 14 and searched by a test start module 331 of the control terminal 3 such that a precise fitting can be performed immediately using the prepared hearing test information if the hearing test is not necessary.

The maximum audible value storing module is a component to store a magnitude of the maximum signal which is audible to user without discomfort, allows to store by frequencies. As described above, the maximum audible value audible to the hearing aid user means the volume of sound when the excessive signal is input from the control terminal 3 during outputting gradually increased signal from the signal variation module 163, and is a magnitude value of Tmax(f) in FIG. 7. Thus, the sound signal at a corresponding frequency is output after always correcting below the maximum audible value such that the user cannot be startled from a loud sound or an ears is prevented from damage. The maximum audible value stored by the maximum audible value storing module 173 is stored in the memory 14.

Figure 8:
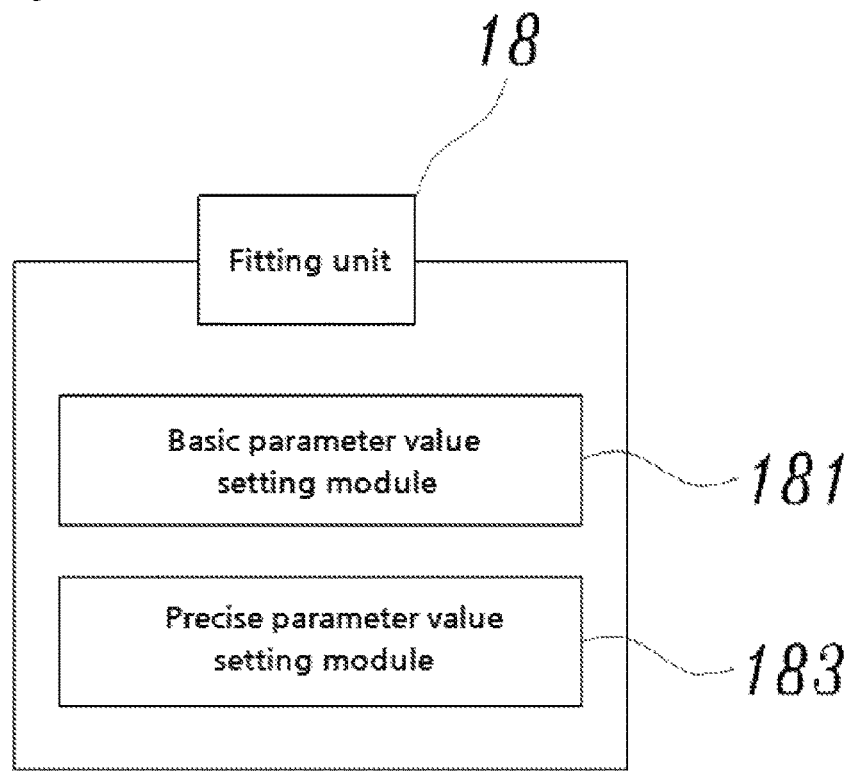
FIG. 8 is a block diagram illustrating a fitting unit of FIG. 3.

The fitting unit 18 is a component to allow fitting of sounds in accordance with user's hearing ability, i.e., the maximum audible value and the minimum audible value, to allow fitting using only the result of the hearing test and to allow more precise fitting of sounds after performing additional precise fitting by the control terminal 3. As shown in FIG. 8, the fitting unit 18 includes a basic parameter value setting module 181 determining parameters of the output signal from the hearing aid in accordance with average value of the minimum audible value and maximum audible value and a precise parameter value setting module 183 determining the parameters of the output signal from the hearing aid after performing additional precise fitting.

The basic parameter value setting module 181 is a component to allow the fitting of the sound using the hearing information tested by the hearing test unit 33, i.e., the maximum audible value and the minimum audible value, and may be selected when there is not enough time to the precise fitting or relatively accurate sound is audible in a silent circumstance without performing the precise fitting. The basic parameter value setting module 181 calculates the average value of the minimum audible value and maximum audible value stored by the minimum audible value storing module 171 and the maximum audible value storing module 173, and allows the sound from the receiver 13 of the hearing aid to output in accordance with the average value of the minimum audible value and the maximum audible value. Thus, the sound from the hearing aid 1 can be output appropriately within the range of audible to users in comfortable. The basic parameter value set by the basic parameter value setting module 181 is stored in memory 14. The sound is processed by the signal processor 12 in accordance with the basic parameter value such that the sound by frequency can be always output in correspond with the average value of the minimum audible value and the maximum audible value. The basic parameter value setting module 181 may not set the average value of the minimum audible value and the maximum audible value as the basic parameter value, but a corresponding sound value as the basic parameter value after making data from sounds of audible volume for common people with hearing ability of corresponding range. The hearing aid 1 can be composed to output sounds that common people having hearing ability of the measured minimum audible value and maximum audible value can hear best in the range.

The precise parameter value setting module 183 is a component to set a precise parameter value in order to output sound further precisely fitted by a precise fitting unit 35 of the control terminal 3. The precise fitting unit 35 measures sounds by frequency which is audible to user in most comfortable. The precise parameter value setting module 183 sets parameter in order that the hearing aid 1 always outputs sound audible to user in comfortable. Thus, the precise fitting unit 35 outputs sounds at a smaller unit than the sounds during the hearing test to search the sound that user can hear most comfortably, the precise parameter value setting module 183 adjusts parameter, sets and store in order to always output at the selected magnitude by the a optimum selection module 355 of the precise fitting unit 35. The precise fitting unit 35 can select optimal sounds by frequencies such that the optimal sounds by frequencies is output and the user can always hear the comfortable sound from the hearing aid. The precise fitting unit 35 will be described hereinafter.

Figure 9:
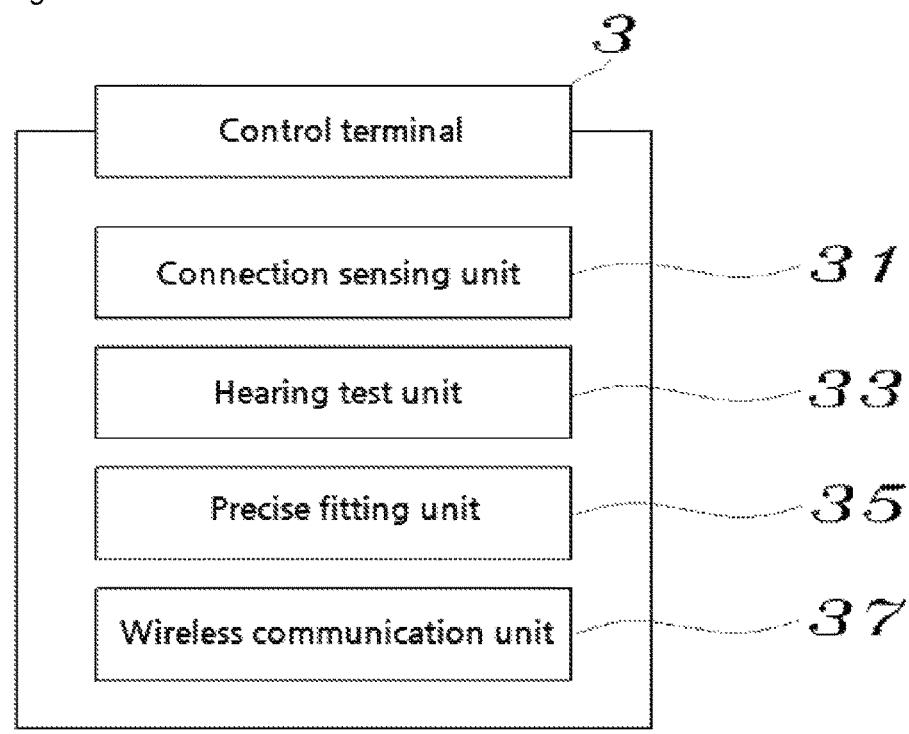
FIG. 9 is a block diagram illustrating a control terminal of FIG. 2.

The control terminal 3 is a component to transmit audibility of sounds to the hearing aid 1 and perform various controls in order to allow the self-hearing test and self-fitting for the hearing aid. The variety of devices such as smartphone, a tablet, a notebook and PC can be applicable to the control terminal 3. Thus the user of the hearing aid can perform the hearing test unit and self-fitting very easily whenever and wherever after just installing an application or software into the variety of devices possessed in person. As shown in FIG. 9, the control terminal 3 includes a connection sensing unit 31 sensing connectivity with the hearing aid 1, a hearing test unit 33 transmitting audibility of signals from the hearing aid to test user's hearing ability, a precise fitting unit 35 allowing precise fitting for the hearing aid 1, and a wireless communication unit 37 implementing wireless communication with the hearing aid 1.

The connection sensing unit 31 is a component to sense the hearing aid 1 and allow the wireless communication between the hearing aid 1 and the control terminal 3, and automatically attempt to communicate with the wireless communication unit 15 of the hearing aid 1 through the wireless communication unit 37 and connect each other when the application or the software for the hearing test and fitting for the hearing aid 1 is executed.

Figure 10:
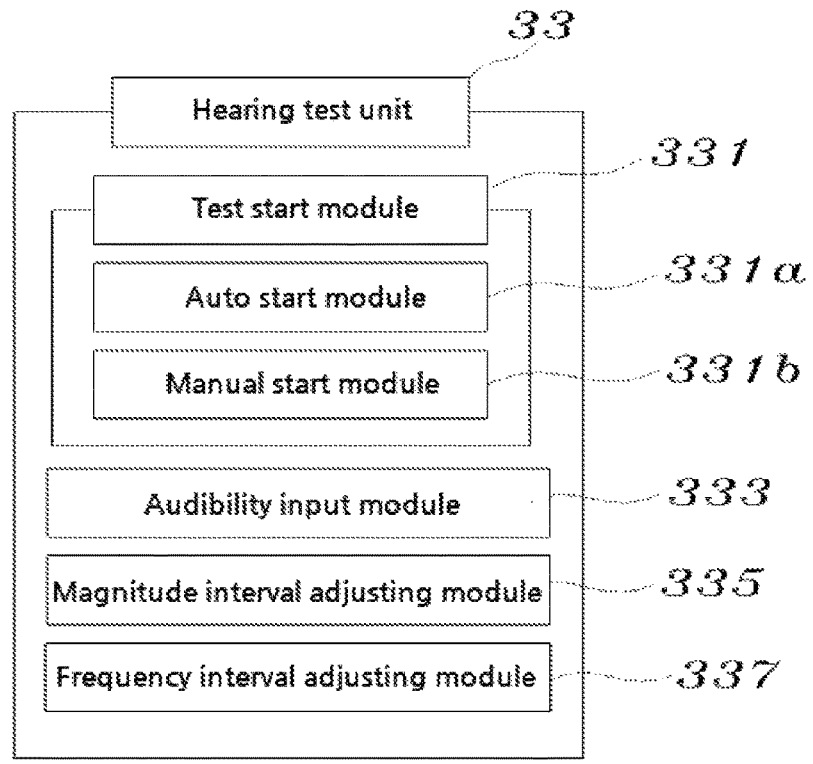
FIG. 10 is a block diagram illustrating a hearing test unit of FIG. 9.

The hearing test unit 33 is a component to measure the hearing ability while the user is wearing the hearing aid 1, and allows inputting audibility after hearing the signal generated from the signal generating unit 16 of the hearing aid 1 when the hearing test is started. Therefore, the user input through the control terminal 3 whether the signal is audible, inaudible or too loud audible to transmit the signal to the hearing aid 1. As described above, the minimum audible value and maximum audible value and etc. which is audible to the user are stored according to the user's input signal thereby performing the sound fitting. As shown in FIG. 10, the hearing test unit 33 includes a test start module 331 starting the hearing test, an audibility input module 333 inputting and transmitting audibility of the sound generated from the signal generating unit 16 of the hearing aid 1 through the hearing aid 1, a magnitude interval adjusting module 335 adjusting the magnitude interval of the sound from the signal generating unit 16, and a frequency interval adjusting module 337 adjusting the frequency interval of the sound generated from the signal generating unit 16.

The test start module 331 is a component to start output of sound for hearing test by the signal generating unit 16 of the hearing aid 1, and searches the memory 14 of the hearing aid 1 to sense that the user's hearing information is stored. The test start module 331 determines that the hearing test has been already performed and inquires whether the hearing test starts or not when there is stored minimum audible value and maximum audible value after searching the minimum audible value and the maximum audible value stored in the memory 14, and continues the fitting using the stored minimum audible value and maximum audible value if the user select not to perform the hearing test. The test start module 331 includes an auto start module 331a starting the hearing test automatically and a manual start module 331b starting the hearing test in manual.

The auto start module 331a is a component to starting automatically output of the sound signal by the signal generating unit 16, searches the memory 14 of the hearing aid 1, determines that the hearing test has not been performed if there is no the minimum audible value and the maximum audible value in the memory 14, and starts output of the sound by the signal generating unit 16 automatically. If the sound are starting to output by the signal generating unit 16, the audibility input module 333 inputs audibility of the sound through the control terminal 3.

The manual start module 331b is a component to start the hearing test in manual, searches the memory 14 of the hearing aid 1, determines that the hearing test has been performed if there are the minimum audible value and the maximum audible value in the memory, and inquires the user whether the hearing test starts or not. The sound is starting to output by the signal generating unit of the hearing aid if the start of the hearing test is selected by user's selection, and the fitting is performed using the stored minimum audible value and maximum audible value if the omission of the hearing test is selected.

Figure 11:
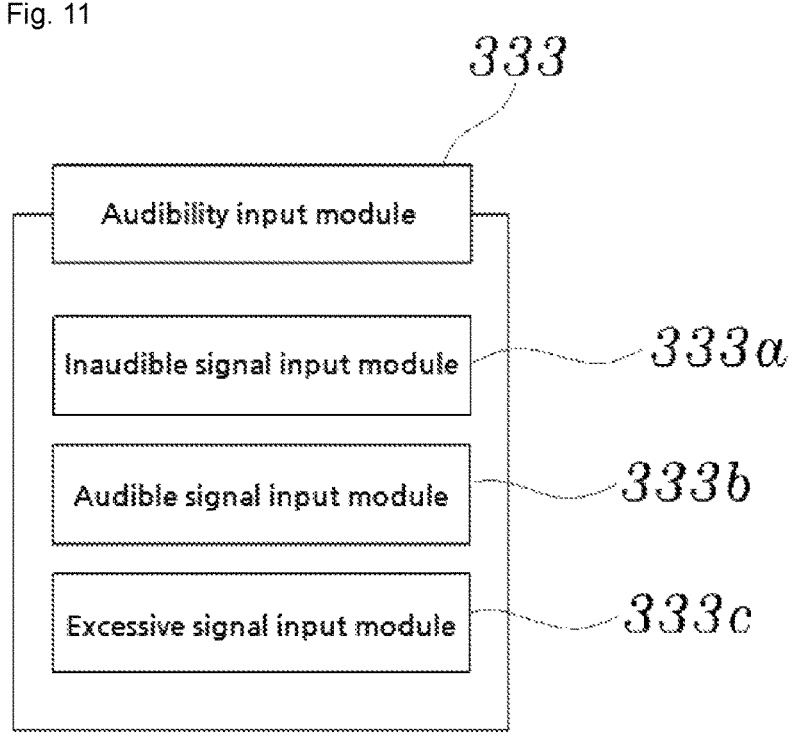
FIG. 11 is a block diagram illustrating a hearing input module of FIG. 10.

The audibility input module 333 is a component to input and transmit audibility of the signal generated by the signal generating unit 16 if the hearing test starts by the test start module 331, as shown in FIG. 11, includes an inaudible signal input module 331a which transmits a signal indicating inaudibility, an audible signal input module 331b which transmits a signal indicating audibility and an excessive signal input module 331c which transmits a signal indicating excessive audibility. The audibility input module 333 is formed into touching on a display of the control terminal 3 or pressing a button. The signal generating unit 16 is starting to output minimum signal audible to common people at a specific frequency if the hearing test start, and the user presses a specific button or touches the display to transmit the inaudible signal if the sound is inaudible. If the inaudible signal is transmitted to the hearing aid 1 by the inaudible signal input module 331a, the signal generating unit 16 outputs increased signal at a regular interval by the signal variation module 163 again and the audible signal is transmitted to the hearing aid 1 by the audible signal input module 331b to store corresponding magnitude of the signal as the minimum audible value of corresponding frequency if user inputs a signal indicating audible at first while this process is repeated. The signal generating unit 16 simultaneously outputs signals which are continuously increased, the excessive signal input module 331c transmits the excessive signal to the hearing aid 1 if the excessive signal is input by the user, and the audibility storing unit 17 of the hearing aid 1 stores the signal as the maximum audible value of the user. Then, the signal generating unit 16 changes the frequency by the signal generating unit by frequency module 161 to repeat the above process, and measures and stores the minimum audible value and the maximum audible value at the corresponding frequency. If all of the minimum audible value and maximum audible value over predetermined frequencies after repeating this process, the stored minimum audible value and maximum audible value set a range of sound output by frequency and becomes a reference value of the basic parameter value setting module 181 thereby setting the fitting range of the precise fitting unit 35.

The magnitude interval adjusting module 335 is a component to adjust a magnitude interval of the signal from the signal generating unit 16. The signal generating unit 16 outputs signals increasing at a regular interval from a minimum signal audible to common people when the hearing test starts (as described above, the signals may be output decreasing from high signal). The magnitude interval adjusting module 335 adjust the magnitude interval of the output signal such that a precise hearing test or a fast hearing test can be performed occasionally in accordance with circumstances and user's hearing characteristics.

The frequency interval adjusting module 337 is a component to adjust a frequency interval of the signal from signal generating unit 16. As described above, the signal generating unit 16 generates signals of regular magnitude interval by frequency using the signal generating by frequency unit 161. The frequency interval adjusting module 337 adjusts the frequency interval of the signal such that the precise hearing test and the fast hearing test can be performed as occasion arises. This relates to performance of the hearing aid 1.

Figure 12:
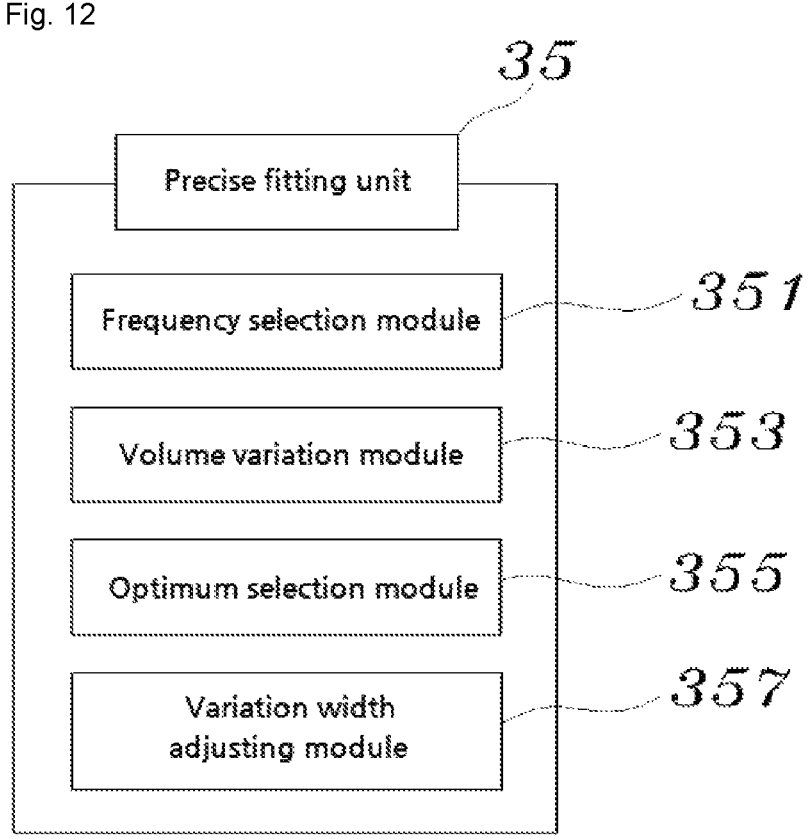
FIG. 12 is a block diagram illustrating a precise fitting unit of FIG. 9.

The fitting unit 35 is a component to perform further precise fitting of the hearing aid 1 in basis of the user's hearing ability measured by the hearing test unit 33, and selects the most audible sound for the user between the minimum audible value and the maximum audible value stored in the memory 14 after measuring by the hearing test unit 33 such that precise fitting can be performed. The precise fitting unit 35 includes, as shown in FIG. 12, a frequency selection module 351 selecting a frequency for the precise fitting, a volume variation module 353 increasing or decreasing volume at the frequency selected by the frequency selection module 351, an optimum selection module 335 selecting the most audible sound, and a variation width adjusting module 357 adjusting an increasing interval of the volume.

The frequency selection module 351 is a component to select a frequency for the precise fitting, selects a frequency from frequencies of which the minimum audible value and the maximum audible value are stored by the hearing test unit 33, and searches a magnitude of the most audible sound between them. If the precise fitting is performed for a certain frequency, the precise fitting is performed to other frequencies. As a result, the precise fitting can be performed to all of the frequencies of which the minimum audible value and the maximum audible value are stored.

The volume variation module 353 is a component allowing the signal generating unit 16 of the hearing aid to output a signal with increasing or decreasing magnitude at regular intervals at the frequency selected by the frequency selection module 351. The volume may increase of decrease in accordance with touching display or pressing button by the user. The sound output by the volume variation module 353 is performed between the minimum audible value and the maximum audible value. It is regardless to start the sound output at any value from the minimum audible value and the minimum audible value. Therefore, the user can hear sounds between the minimum audible value and the maximum audible value which is increased or decreased by the volume variation module 353, and selects the most audible sound.

The optimum selection module 355 is a component to select the most audible sound with adjusting the sound from the hearing aid 1 by the volume variation module 353, and select the sound in accordance with touching display or pressing button by the user. If the most audible sound is selected by the optimum selection module 355, the precise parameter value setting module 183 of the hearing aid 1 sets a precise parameter value on the basis of corresponding volume such that an optimum sound can be output. In other words, if sounds by frequencies are selected, parameters adjusting the volume of most audible to the user at each frequency are set and stored thereby the optimum sound can be always output from the hearing aid 1. Thus, the hearing aid 1 according to the present invention sets and store the parameters by the sound actually heard from the hearing aid 1 such that the optimum sound can be output in constant. And, the hearing test and the precise fitting can be performed using the control terminal 3 easily such that the fitting of the hearing aid can be performed occasionally for variation of the hearing ability and circumstances.

The variation width adjusting module 357 is a component to adjust the volume interval increased or decreased by the volume variation module 353. The fitting time is decreasing but detail is lowing as enlarging the variation width. In contrast, the fitting time is increasing but more detailed fitting is possible as narrowing the variation with. Thus, the user can select appropriated variation width in accordance with the hearing impediment or circumstances such that the precise fitting can be performed.

The wireless communication unit 37 is a component to wireless communication unit communicate with the wireless communication unit 15 of the hearing aid 1, may be a Bluetooth, BLE (Bluetooth Low Energy), WIFI and so on.

A method of self-hearing test and fitting using the system of self-hearing test and fitting according to an embodiment of the present invention will be described. The method of self-hearing test and fitting includes a connecting step Si of connecting the control terminal 3 and the hearing aid 1, a test starting step S2 of determining start of the hearing test, a hearing test step S3 of performing the hearing test, and a fitting step S4 of performing fitting on the basis of user's hearing information measured in the hearing test step S3.

The connecting step S1 is a step of sensing the hearing aid 1 by the connection sensing unit 31 of the control terminal 3 and connecting each other. The hearing aid 1 and the wireless communication unit 15, 37 of the control terminal 3 are connected to transmit a signal for the hearing test and the fitting.

The test starting step S2 is a step of determining whether the hearing test is to be performed or not. The test start module 331 of the control terminal 3 ascertains that the hearing test information, i.e., the minimum audible value and the maximum audible value is stored in the memory 14, and the auto start module 331a implements the hearing test automatically S21 if the information is not stored or the manual start module 331b inquires to user whether the hearing test is to be performed or not S22 if the stored minimum audible value and the maximum audible value exist. The hearing test starts if the user selects the start of the hearing test and the fitting is performed by the previously stored minimum audible value and maximum audible value if the start of the hearing test is not selected. Although a record of the hearing test exists, the user selects the start of the hearing test to perform the hearing test when the user wants to perform the hearing test again because of changing the hearing ability as time passed and various occasions.

Figure 14:
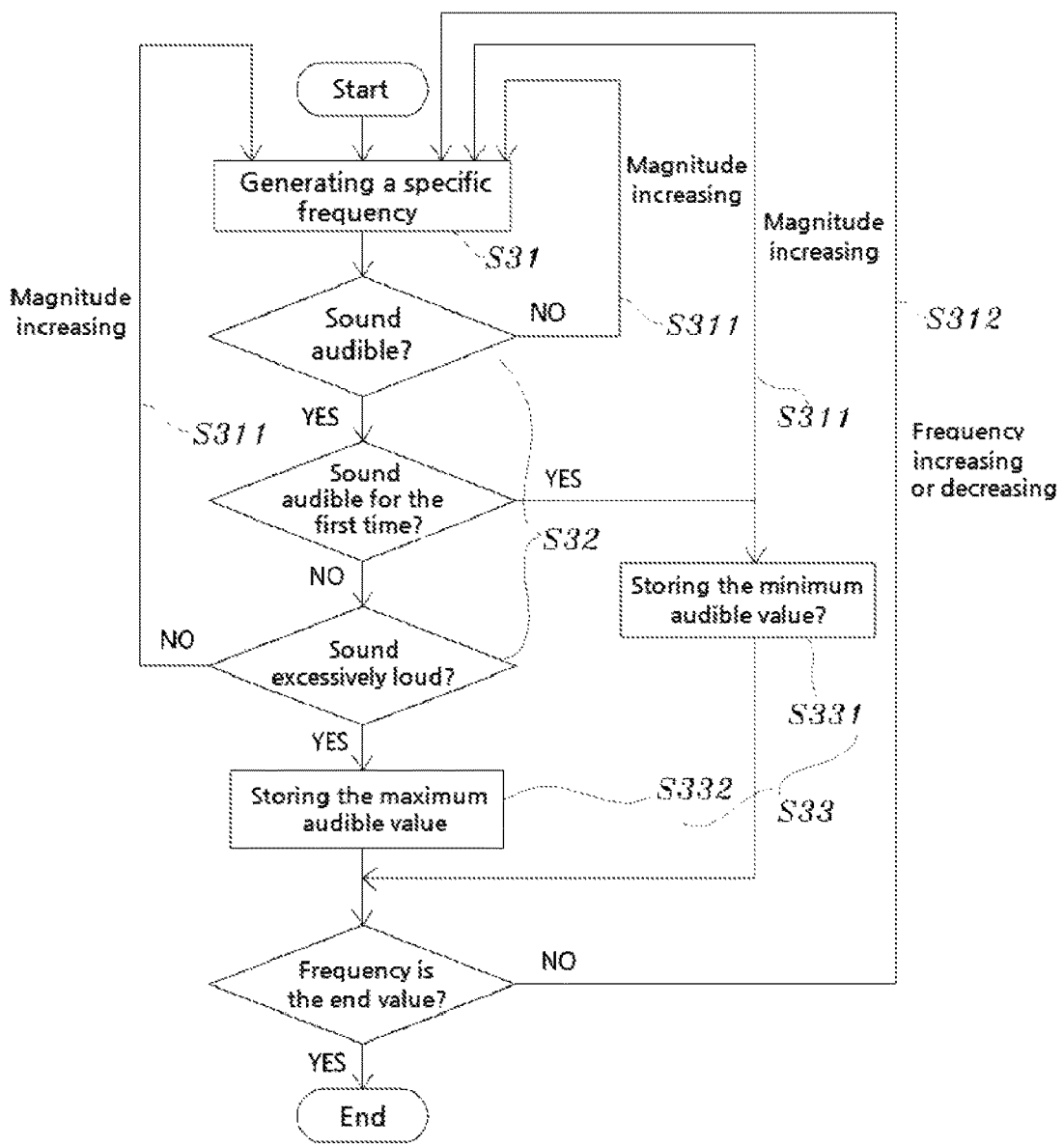
FIG. 14 is a flow diagram illustrating process of hearing test steps of FIG. 13.

The hearing test step S3 is a component for performing the hearing test in accordance with control of the control terminal 3 while the user is wearing the hearing aid 1, more specifically, for measuring by frequency the minimum audible value audible to the user and the maximum audible value audible to the user without discomfort such that an audible range of the user can be measured. The hearing test step S3 includes, as shown in FIG. 14, a signal generating step S31 of generating a signal with regular magnitude at a specific frequency, a audibility inputting step S32 of inputting and transmitting whether the signal generated in the signal generating step 31 is audible or not, and a hearing storing step S33 of measuring and storing the minimum audible value and the maximum audible value of the user in accordance with audibility to the user.

The signal generating step S11 may start by outputting a signal with minimum magnitude audible to common people at a specific frequency. The user determines whether the sound is audible through the hearing aid 1 to input through the control terminal 3. If the inaudible signal is input in the audibility inputting step S32, the signal variation module 163 of the signal generating unit 16 outputs the signal after increasing magnitude S311, and the volume is increasing until the audible signal is input S311. If the audible signal is input by the control terminal 3 after hearing a sound at first, the magnitude of the signal is stored in the memory 14 of the hearing aid as the minimum audible value and the signal generated from the signal generating unit 16 increasing continuously S311. If the user feels discomfort about too loud sound to input the excessive signal, the magnitude of the signal is stored as the maximum audible value, and the signal generating unit 161 changes the frequency S312 such that the same process is repeated from the signal audible to the common people.

The audibility inputting step S32 is a step that user inputs the inaudibility, audibility or excessiveness using the control terminal 3 in accordance with the signal generated in the signal generating step S31. As described above, the user's hearing ability is stored in accordance of the user's input, in the hearing storing step S33.

The hearing storing step S33 is a step of measuring the user's minimum audible value and maximum audible value and storing in the memory 14, includes a minimum audible value storing step S331 and a maximum audible value storing step S332. As described above, the minimum audible value storing step S331 stores the magnitude of the signal when the audible signal is input at first in the audibility inputting step S32, and the maximum audible value storing step S332 stores the magnitude of the signal when the excessive signal is input through the control terminal 3 in the audibility inputting step S32.

The fitting step S4 is a step of fitting the sound output from the hearing aid 1 in accordance with the user's hearing ability, i.e., the minimum audible value and the maximum audible value measured and stored in the hearing test step S3, and includes a basic fitting step S41 in which the fitting is performed using the minimum audible value and the maximum audible value only and the precise fitting step S42 in which additional precise fitting is performed.

The basic fitting step S41 is a step of setting and storing the basic parameter value by the basic parameter value setting module 181 of the fitting unit 18. The parameter value of the hearing aid 1 is fitted in order to perform the output of the hearing aid 1 in accordance with the average value continuously. Therefore, the hearing aid 1 may output a sound within an audible range for the user continuously though it is not precise. As described above, the basic parameter value setting module 181 may set the most audible value as the basic parameter value after making database with a value of the most audible sound within a corresponding range for the common people with the corresponding range, without using the average value of the minimum audible value and the maximum audible value.

Figure 13:
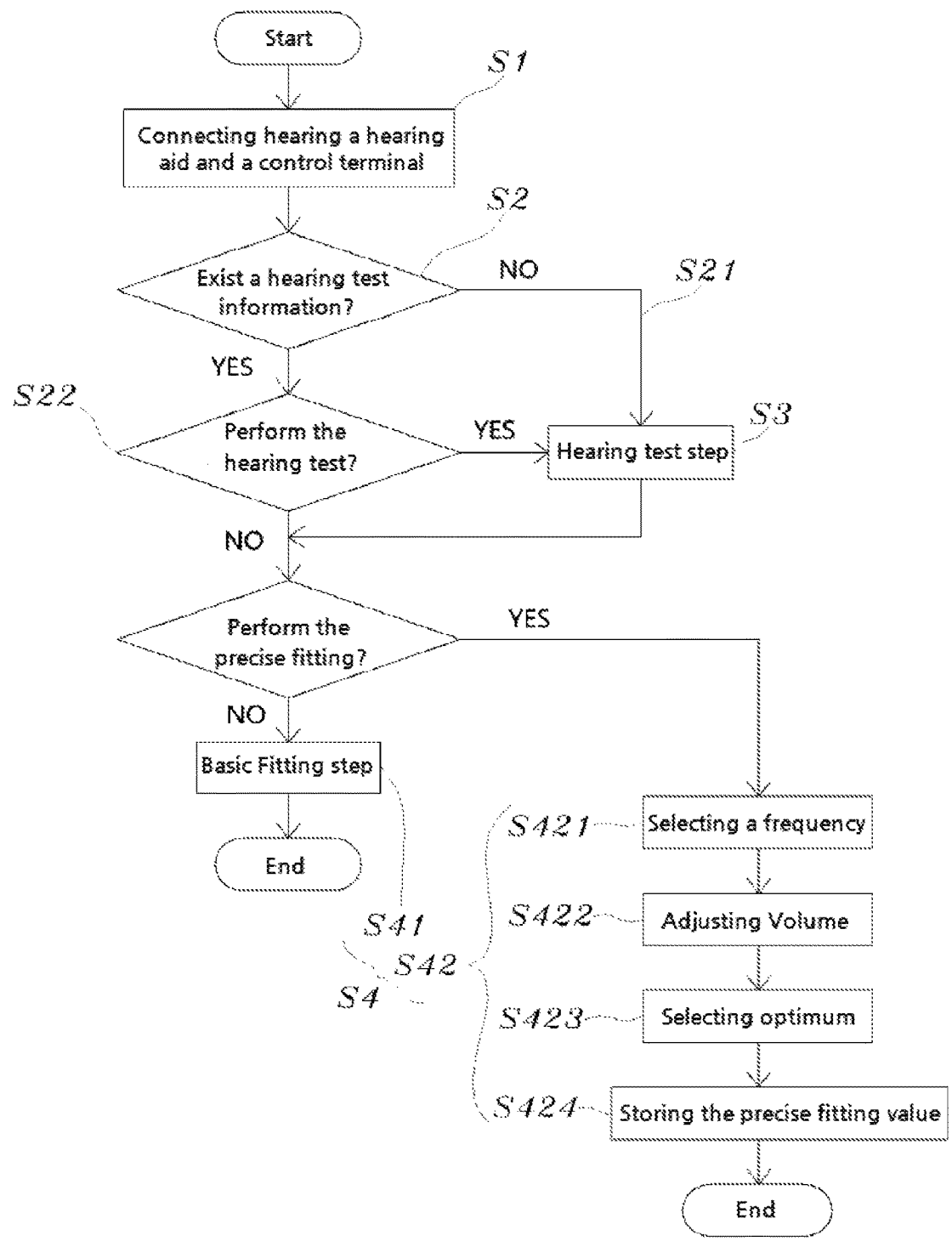
FIG. 13 is a structure drawing illustrating self-hearing test and fitting methods according to another embodiment of the present invention.

The precise fitting step S42 is a step of performing additional precise fitting on the basis of the hearing information of the user measured in the hearing test step S3, as shown in FIG. 13, includes a frequency selecting step S421 of selecting a frequency for the precise fitting, a volume variation step S422 of increasing or decreasing a volume output at the frequency selected in the frequency selecting step S421, an optimum selecting step S423 of selecting the most audible sound while increasing and decreasing the sound in the volume variation step S422, and a precise fitting value storing step S424 of storing the precise fitting value selected in the optimum selecting step S423.

The frequency selecting step S421 is a step of selecting a frequency for the precise fitting by the frequency selection module 315, is preferable to perform the precise fitting at all of the frequencies in which there is the maximum audible value and the minimum audible value measured in the hearing test step S3.

The volume variation step S422 is a step of searching the audible sound with increasing or decreasing the sound at the frequency selected in the frequency selecting step S421. The precise fitting time can be shortened by performing the increasing and the decreasing of the sound within the minimum audible value and the maximum audible value which is measured in the hearing test step S3. The interval of the sound which is increased or decreased in the volume variation step S422 can be increased and decreased by the variation width adjusting module 357.

The optimum selecting step S423 is a step of selecting the most audible sound for the user while the sound is increasing and decreasing in the volume variation step S422. It is selected by touching the display or pressing a button of the control terminal 3, and the magnitude value of the signal is set as an optimum value at the frequency.

The precise fitting value storing step S424 is a step of setting a parameter value such that the hearing aid outputs continuously a sound with constant magnitude after storing a value selected as the most audible sound in the optimum selecting step S424. Optimum sounds by frequency are selected and stored, and the parameter value is set and stored by the precise parameter value setting module 183. Therefore, the hearing aid 1 always output the most audible sound for the user.

In the above, the applicant described various embodiments of the present invention, however, these embodiments are no more than examples for achieving the inventive concept of the present invention, and it should be understood that any modification and regulation of the inventive concepts of the present invention may belong to the scopes of the inventive concepts.

The invention claimed is:

1. A system allowing a self-hearing test and fitting comprising:
  a hearing aid allowing self-hearing test and fitting capable of testing a user's hearing ability comprising:
    a microphone receiving an input,
    a signal processor processing a signal from the input of the microphone,
    a receiver reproducing the signal processed by the signal processor,
    a memory storing various data necessary for operation of the hearing aid,
    a wireless communication unit communicating a wireless signal, the wireless communication unit having an external terminal,
    a signal generating unit receiving a command from the external terminal to let the receiver generate a signal of a predetermined frequency with a predetermined magnitude, and
    a hearing storing unit receiving from the external terminal audibility of the signal generated from the signal generating unit and storing user's hearing ability; and
  a control terminal capable of communicating with the hearing aid and transmitting audibility of the sounds from the hearing aid, the control terminal comprising:
    a connection sensor sensing connectivity with the hearing aid, and a hearing test unit transmitting audibility of signal from the hearing air to test the user's hearing ability, the hearing test unit comprising:
  an audibility input module inputting audibility of the sounds generated from the signal generating unit, the audibility input module comprising:
    an inaudible signal input module which inputs inaudibility indicating that sounds from the signal generating unit are not audible,
    an audible signal input module which inputs audibility indicating that sounds from the signal generating unit are audible, and
    an excessive signal input module which inputs excessiveness indicating that sounds from the signal generating unit are excessive, and
  a precise fitting unit allowing precise fitting for the hearing aid,
wherein the hearing aid receives a sound to transmit after transforming into a sound audible for the user and the hearing test unit stores in the hearing aid a minimum audible value audible to the user and a maximum audible value audible without discomfort to the user which is determined less than the excessiveness inputted b the excessive signal input module.

2. The system of claim 1, wherein the hearing test unit further comprises:
  a magnitude interval adjusting module adjusting a magnitude interval of a signal generated from the signal generating unit, and a frequency interval adjusting module adjusting a frequency interval of the signal generated from the signal generating unit.

3. The system of claim 1, wherein the hearing test unit further comprises:
  a search start module searching hearing test information stored in a memory of the hearing aid to determine a start of hearing test in accordance with existence of the hearing test information.

4. The system of claim 1, wherein
the precise fitting unit selects the most audible sound between the minimum audible value and the maximum audible value.

5. The system of claim 4, wherein the precise fitting unit comprises:
  a frequency selection module selecting a frequency for the precise fitting, a volume variation module increasing or decreasing a volume of the frequency selected by the frequency selection module, and an optimum selection module selecting the most audible sound,
  wherein the fitting unit of the hearing aid comprises a precise parameter value setting module which sets precise parameter value according to the volume selected by the optimum selection module.

6. The system of claim 1, wherein the hearing storing unit comprises:
  a minimum hearing value storing module storing the minimum hearing signal audible to the user of the hearing aid, and a maximum hearing value storing the module storing maximum hearing signal audible to the user of the hearing aid.

7. The system of claim 6, further comprising:
  a fitting unit fitting output of the sound in accordance with user's hearing ability stored in the hearing storing unit.

8. The system of claim 7, wherein the fitting unit comprises:
  a basic parameter value setting module setting parameter value of output from the hearing aid in accordance with the average value of a maximum audible value and a minimum audible value stored by a maximum audible value storing module and a minimum audible value storing module.

9. The system of claim 1, wherein the signal generating unit comprises:
  a signal generating by frequency module generating signals by frequency, and a signal variation module increasing or decreasing at regular intervals magnitude of signals generated by frequency.

* * * * *

UNITED STATES PATENT AND TRADEMARK OFFICE
CERTIFICATE OF CORRECTION

PATENT NO. : 10,455,337 B2  
APPLICATION NO. : 15/562316  
DATED : October 22, 2019  
INVENTOR(S) : Jung Gee Yoo Page 1 of 1

It is certified that error appears in the above-identified patent and that said Letters Patent is hereby corrected as shown below:

In the Drawings

Figure 3:
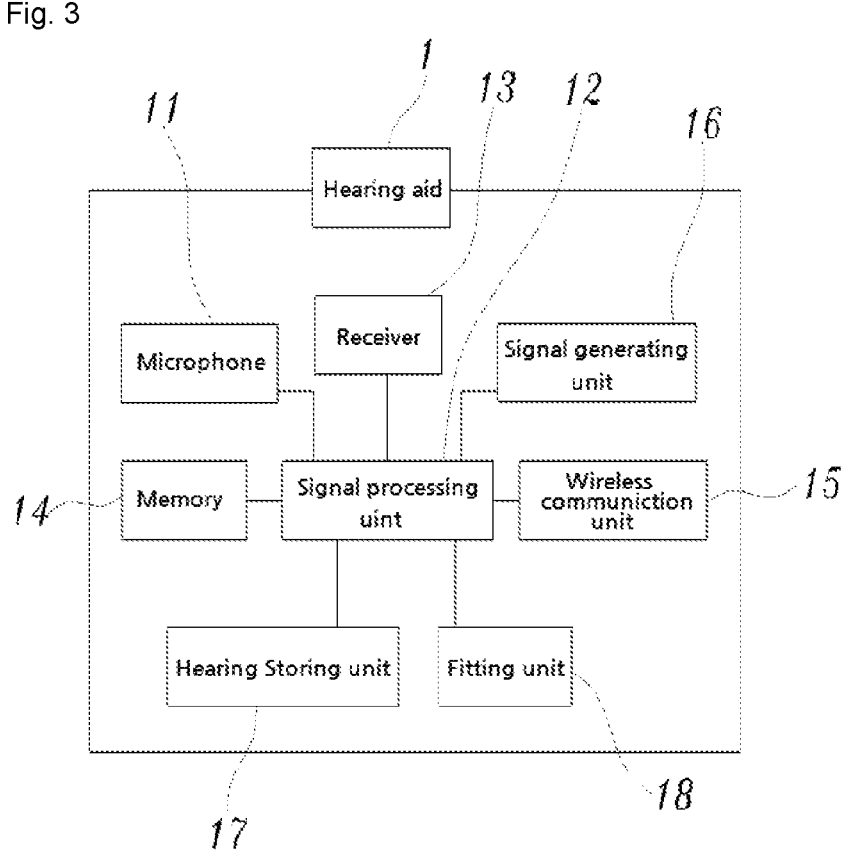
FIG. 3 is a structure drawing of a hearing aid of FIG. 2.
Figure 4:
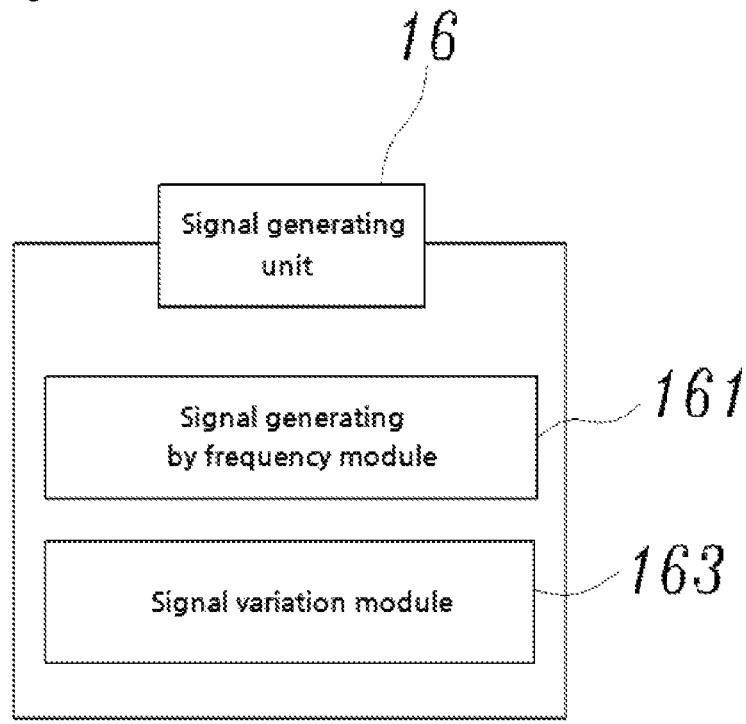
FIG. 4 is a block diagram illustrating a signal generating unit of FIG. 3.

In Fig. 3, Box 12, replace "uint" with "unit".

In Fig. 3, Box 15, replace "communiction" with "communication".

In Fig. 6, Box 17, replace "Sotring" with "Sorting".

In the Claims

In Claim 1, Column 19, Line 26, replace the letter "b" with the word "by".

Signed and Sealed this
Fourteenth Day of January, 2020

Andrei Iancu
*Director of the United States Patent and Trademark Office*